US00PP26525P3

(12) United States Plant Patent
Bacon

(10) Patent No.: US PP26,525 P3
(45) Date of Patent: Mar. 22, 2016

(54) PEACH TREE NAMED 'SUPECHNINETEEN'

(50) Latin Name: *Prunus persica*
Varietal Denomination: Supechnineteen

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 106 days.

(21) Appl. No.: 14/120,635

(22) Filed: Jun. 11, 2014

(65) Prior Publication Data

US 2015/0366116 P1 Dec. 17, 2015

(51) Int. Cl.
*A01H 5/00* (2006.01)

(52) U.S. Cl.
USPC ..... Plt./195

(58) Field of Classification Search
USPC ..... Plt./194, 195
See application file for complete search history.

*Primary Examiner* — Susan McCormick Ewoldt
(74) *Attorney, Agent, or Firm* — Knobbe, Martens, Olson & Bear, LLP

(57) ABSTRACT

A new and distinct peach tree variety, *Prunus persica,* cv. 'Supechnineteen' is characterized by fruit with large size.

1 Drawing Sheet

Latin name of the genus and species claimed: *Prunus persica.*

Variety denomination: 'Supechnineteen'.

BACKGROUND AND SUMMARY OF THE INVENTION

This invention relates to the discovery and asexual propagation of a new and distinct variety of peach, *Prunus persica* cv. 'Supechnineteen'. The new variety was first selected in May 2011 by Terry Bacon as breeder number: 'PE1319W'. The new variety was first evaluated by Terry Bacon near Wasco, Calif. in Kern County. The NEW variety 'Supechnineteen' was originated by hybridization.

The new variety 'Supechnineteen' is characterized by its large size and early ripening.

The seed parent is 'PE921W' (unpatented Sun World peach), and the pollen parent is unknown, being from bulk pollen. The parent varieties were first crossed in February 2008, with the date of sowing being February 2009, and the date of first flowering being February 2011. The new peach variety 'Supechnineteen' was first asexually propagated by Terry Bacon near Wasco, Kern County, Calif. in January 2011, by grafting.

The new variety 'Supechnineteen' is distinguished from its seed parent, 'PE921W', in that the new variety ripens about ten days later than 'PE921W'. 'Supechnineteen' ripens starting about May 3$^{rd}$ compared to April 23$^{th}$ for 'PE921W'. The new variety 'Supechnineteen' also has a larger fruit size at 77 mm fruit diameter compared to 65 mm fruit diameter for 'PE921W'.

The new variety 'Supechnineteen' ripens at nearly the same time as 'Snow Angel' (U.S. Plant Pat. No. 18,750). However, the new variety 'Supechnineteen' has larger sized fruit, at about 77 mm compared to 64 mm for 'Snow Angel'. The new variety 'Supechnineteen' has similar fruit size as 'Spring Snow' (U.S. Plant Pat. No. 9,883) but ripens 20 days earlier.

The new variety 'Supechnineteen' has been shown to maintain its distinguishing characteristics through successive asexual propagations by, for example, budding and grafting.

BRIEF DESCRIPTION OF THE DRAWING

The accompanying color photographic illustration shows typical specimens of the foliage and fruit of the present new peach variety 'Supechnineteen'. The illustration shows the upper and lower surface of the leaves and exterior and sectional views of the fruit. The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1986.

The descriptive matter which follows pertains to 3 year old 'Supechnineteen' trees on Nemared (unpatented) rootstock, grown in the vicinity of Wasco, Kern County, Calif., during 2014, and is believed to apply to plants of the variety grown under similar conditions of soil and climate elsewhere.

TREE

General: (Measurements taken on 3 year old trees unless otherwise noted.).

*Size.*—Medium. Normal for most peach varieties. Reaches a height of approximately 3 meters with normal pruning.

*Spread.*—Normal for most peach varieties. Approximately 3 meters with normal pruning.

*Vigor*.—Moderately vigorous; growth of about 1.8 to about 2 meters in height during the first growing season.

*Growth*.—Semi-upright.

*Productivity*.—Productive. Fruit set is usually two or more times the desired amount for marketable size fruit; thinning and spacing of fruit is necessary.

*Form*.—Vase formed.

*Bearer*.—Regular.

*Fertility*.—Self-fertile.

*Canopy density*.—Dense.

*Hardiness*.—Hardy in all fruit growing areas of California; winter chilling requirement is approximately 200 hours at or below 7.2° C.

*Disease resistance/susceptibility*.—No specific testing for relative plant disease resistance/susceptibility has been undertaken. Under close observation in Kern County, California, no particular plant/fruit disease resistance/susceptibility has been observed.

Trunk: (Measurements at approximately 30 cm above soil line.).

*Diameter*.—Approximately 18 cm.

*Texture*.—Medium shaggy, increases with age of tree.

*Trunk color*.—Outer bark about Light Greyed-green 197D to about Dark Greyed-green 197A; inner bark about Dark Greyed-orange 177A to about Medium Greyed-orange 174B.

Branches: (Measurements at approximately 90 cm above soil line.).

*Size*.—Approximately 10 cm.

*Texture*.—Medium shaggy; increasing with tree age.

*Color*.—About Light Greyed-green 197D to about Medium Greyed-orange 166D.

*Number of lenticels*.—Medium.

*Lenticels density*.—Approximately 2-4 per $cm^2$.

*Lenticels color*.—About Medium Greyed-orange 166D.

*Lenticels size*.—Medium.

*Lenticels length*.—Approximately 3 mm.

*Lenticels width*.—Approximately 1.5 mm.

Flowering shoots: (Data taken in June at midpoint of current-season growth.).

*Size*.—Average diameter approximately 5 mm.

*Color*.—Topside: About Light Yellow-green 145A. Underside: About Light Yellow-green 145A.

*Internode length*.—Medium; approximately 3 cm. Midway on flowering shoot.

*Flowering shoot lenticels*.—Sparse. Color: About Medium Yellow-green 148B. Diameter: Approximately 0.3 mm.

*Flowering shoot leaf buds*.—Shape: Elliptic to conical. Width: Approximately 3 mm. Length: Approximately 4 mm. Color: About Medium Greyed-green 197C.

*Flowering shoot flower buds*.—Shape: Conical. Width: Approximately 25 mm. Length: Approximately 4 mm. Color: About Medium Greyed-green 197C. Number of buds per node: Usually 2.

*Flower bud hardiness*.—Medium-hardy.

*Internode length*.—Medium, about 3 cm midway of flowering shoots.

*Density of buds*.—Medium.

*Flower bud distribution*.—Generally isolated in groups of 2 on one year old shoots.

*Ratio of wood (leaf) buds to flowering shoots*.—½.

FOLIAGE

Leaves: (Data taken in June on fully expanded leaf at midpoint of current-season growth.).

*Size*.—Medium.

*Average length*.—Medium; approximately 10-14 cm.

*Average width*.—Medium; approximately 3-4 cm.

*Thickness*.—Medium.

*Color*.—Upper Surface: About Dark Yellow-green 147A. Lower Surface: About Medium Yellow-green 147B.

*Form*.—Lanceolate.

*Tip*.—Cuspidate.

*Base*.—V-shaped.

*Margin*.—Crenate.

*Venation*.—Pinnately veined.

*Vein color*.—About Medium Yellow-green 148C.

*Surface texture*.—Smooth.

*Leaf blade (ratio of length to width)*.—Medium; about 4/1.

*Shape in the cross section*.—Concave.

*Angle at apex*.—Medium.

*Profile*.—Up folded.

*Leaf blade tip*.—Curved downwardly.

*Angle of tip*.—Acute.

*Undulation of margin*.—Slight.

Petiole:

*Average length*.—Medium; approximately 11 mm.

*Average diameter*.—Approximately 2 mm.

*Color*.—About Medium Yellow-green 148C.

Stipules:

*Number/leaf bud*.—Approximately 2.

*Typical length*.—Approximately 7 mm.

*Color*.—About Dark Greyed-orange 176A when dry.

*Persistence*.—Falls off.

Leaf glands:

*Form*.—Reniform.

*Average number*.—Between about 0 and 4; usually 2.

*Position*.—On both leaf base and petiole, alternate.

*Average size*.—Medium; approximately 1 by 1.5 mm.

*Color*.—About Medium Yellow-green 144B.

FLOWERS

General:

*Flower blooming period*.—First Bloom: Approximately February 7. Full Bloom: Approximately February 10.

*Time of bloom*.—Early.

*Location of first bloom*.—Lower third of the canopy.

*Location of full bloom*.—Throughout the canopy, fully opened flowers.

*Duration of bloom*.—Medium; approximately 10 days.

*Type of bloom*.—Non-showy.

*Diameter of fully opened flower*.—Medium, approximately 37 mm.

*Flower aroma*.—Slight aroma.

*Shape*.—Rosaceous.

Peduncle:

*Length*.—Medium; approximately 4 mm.

*Diameter*.—Slender; approximately 1.5 mm.

*Color*.—About Medium Yellow-green 144A.

*Pubescence*.—Absent.

Petals:

*Number*.—5.

*Arrangement*.—Free.

*Length*.—Approximately 13 mm.

*Diameter*.—Approximately 7 mm.

*Shape*.—Elliptic.

*Apex shape*.—Rounded.

*Base shape*.—Narrows, cuneate.
*Color*.—Inner Surface: About Light Red-purple 62B, becoming darker over time. Outer Surface: About Light Red-purple 62B, becoming darker over time.
*Surface texture*.—Smooth.
*Margins*.—Slightly undulating.
*Frequency of flowers with double petals*.—Few to none.
*Petal size*.—Medium.
*Claw*.—Absent.
*Margin waviness*.—Weak.
*Base angle*.—Medium.
*Division of upper margin*.—Entire.
*Pubescence of inner surface*.—Absent.
*Pubescence of outer surface*.—Absent.

Sepals:
*Number*.—5.
*Length*.—Approximately 5 mm.
*Diameter*.—Approximately 3 mm.
*Shape*.—Triangular.
*Color*.—About Medium Red-purple 64B outside surface.
*Surface texture*.—Smooth.
*Margins*.—Entire.
*Positioning*.—Touching petals when opened.
*Pubescence of inner surface*.—Absent.
*Pubescence of outer surface*.—Absent.
*Frequency of flowers with double sepals*.—None.

Stamens:
*Number*.—Many; usually 38-48.
*Average length*.—Approximately 12 mm.
*Filament color*.—About Light Red-purple 62C, darkening to Medium Red-purple 64B as flower ages.
*Anther color*.—About Medium Red-purple 61B.
*Flower pollen color*.—About Dark Yellow-orange 22A when dried.
*Position*.—Perigynous.

Pistil:
*Number*.—Usually one.
*Average length*.—Approximately 18 mm.
*Ovary diameter*.—Approximately 1.5 mm.
*Pubescence*.—None.
*Stigma extension in comparison to anthers*.—Usually with and above.
*Frequency of supplementary pistils*.—Few.

Receptacle:
*Depth*.—Medium.
*Pubescence of inner surface* (*at pink bud stage*).—Absent.
*Pubescence of outer surface*.—Absent.

Ovary:
*Pubescence*.—Slight.
*Density of hairs*.—Dense.

FRUIT

General: (Description taken at firm-ripe on mature tree which obtained maximum quality under conditions stated in the description of the variety. Description taken on May 6, 2009 near Wasco, Kern County, Calif.).
*Harvest*.—Date of First Pick: Approximately May 3. Date of Last Pick: Approximately May 11.
*Maturity when described*.—Firm-mature.
*Season ripening*.—Very early.
*Position of maximum diameter*.—Towards the middle.
*Symmetry about the suture*.—Somewhat symmetric.
*Size*.—Length (Stem End to Apex): Approximately 78 mm. Diameter in Line with Suture Plane: Approximately 78 mm.
*Diameter perpendicular to suture plane*.—Approximately 77 mm.
*Average weight*.—Approximately 205 gm.
*Form*.—Viewed from Apex: Rounded, nearly symmetrical. Viewed from Side, Facing Suture: Rounded, nearly symmetrical. Viewed from Side, Perpendicular to Suture: Rounded, nearly symmetrical.
*Apex shape*.—Rounded.
*Apex base*.—Rounded.

Fruit stem cavity:
*Shape*.—Rounded.
*Depth*.—Medium; approximately 0.8 cm.
*Breadth*.—Approximately 1.5 cm.
*Width*.—Medium.

Fruit stem:
*Length*.—Medium, approximately 9 mm.
*Diameter*.—Approximately 2.5 mm.
*Color*.—About Medium Greyed-orange 164B.
*Adherence to stone*.—Medium.

Fruit skin:
*Thickness*.—Medium.
*Adherence to flesh*.—Strong.
*Surface texture*.—Medium.
*Pubescence*.—Slight.
*Bloom*.—Absent.
*Ground color*.—About White 155A when mature.
*Overcolor*.—About Light Red 39C to Medium Red 53C.
*Taste*.—Neutral.
*Reticulation*.—Absent.
*Roughness*.—Absent.
*Tenacity*.—Tenacious to flesh.
*Tendency to crack*.—None, in wet season.

Flesh:
*Ripens*.—Evenly.
*Texture*.—Firm, melting.
*Fibers*.—Few.
*Flavor*.—Mild.
*Brix*.—Approximately 12°.
*Juice*.—Moderate.
*Aroma*.—Slight.
*Color*.—About White 155A when mature.
*Anthocyanin color of flesh*.—None or weakly expressed.
*Anthocyanin color around stone*.—Absent.
*Amygdalin*.—Wanting
*Acidity*.—Low.
*Sugar content*.—Medium.
*Eating quality*.—Good.
*Stone/flesh ratio*.—About ¼.
*Firmness*.—Firm.

Shape of pistil point: Rounded.

Pit cavity size:
*Length*.—Approximately 28 mm.
*Diameter in line with suture plane*.—Approximately 22 mm.
*Diameter perpendicular to suture plane*.—Approximately 18 mm.
*Color*.—About White 155A.

Fruit use: Fresh market.
Fruit shipping and keeping quality: Good.
Suture line: Inconspicuous.

Stone:

*Stone freeness*.—Cling over the entire surface.

*Degree of adherence to flesh*.—Strong.

*Stone size*.—Medium. Size compared to Fruit: Medium. Length: Medium, approximately 28 mm. Diameter in Line with Suture plane: Approximately 22 mm. Diameter Perpendicular to Suture Plane: Approximately 18 mm. Width of Stalk End: Medium; approximately 3 mm. Angle of Stalk end: Right angle. Hilum: Oval, nearly symmetrical.

*Stone form*.—Viewed from Side: Oval. Viewed from Ventral Side: Oval.

*Stone shape*.—Base shape: Nearly straight. Apex shape: Pointed. Hilum: Oval.

*Stone surface*.—Pitted throughout.

*Stone halves*.—Nearly symmetric.

*Stone ridges*.—Rounded continuous.

*Stone outgrowing keel*.—Partially developed.

*Stone tendency to split*.—Slight in wet season.

*Stone color*.—About Medium Greyed-orange 166C when dried.

*Position of maximum*.—Toward middle.

*Sides*.—Nearly equal.

*Pits*.—Angular.

*Fibers*.—Short.

*Ventrical edge*.—Medium.

*Dorsal edge*.—Narrow grooves, interrupted.

What is claimed is:

1. A new and distinct peach tree as herein described and illustrated.

* * * * *

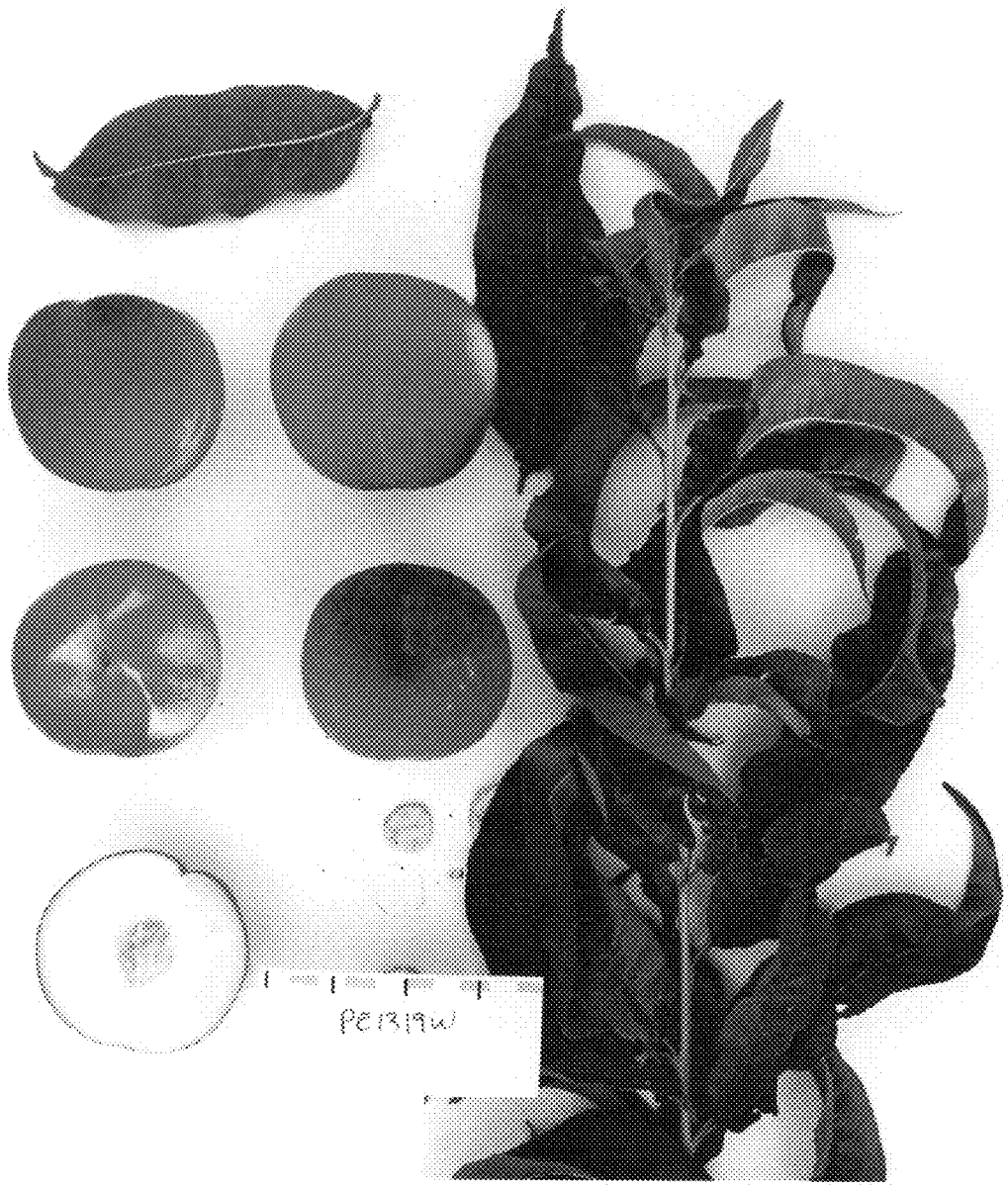
PE8194W